(12) United States Patent
Tweden et al.

(10) Patent No.: US 6,182,668 B1
(45) Date of Patent: Feb. 6, 2001

(54) TRANSMYOCARDIAL IMPLANT WITH INDUCED TISSUE FLAP

(75) Inventors: Katherine S. Tweden, Mahtomedi; Guy P. Vanney, Blaine; Mark B. Knudson, Shoreview, all of MN (US)

(73) Assignee: HeartStent Corporation, St. Paul, MN (US)

(*) Notice: Under 35 U.S.C. 154(b), the term of this patent shall be extended for 0 days.

(21) Appl. No.: 09/311,003

(22) Filed: May 13, 1999

(51) Int. Cl.$^7$ .................................................. A61B 19/00
(52) U.S. Cl. ............................................................... 128/898
(58) Field of Search ........................... 128/898; 623/1.13, 623/1.23, 23.64; 604/7, 8; 606/191

(56) References Cited

U.S. PATENT DOCUMENTS

| | | |
|---|---|---|
| 4,546,499 | 10/1985 | Possis et al. . |
| 5,287,861 | 2/1994 | Wilk . |
| 5,409,019 | 4/1995 | Wilk . |
| 5,429,144 | 7/1995 | Wilk . |
| 5,655,548 | 8/1997 | Nelson et al. . |
| 5,755,682 | 5/1998 | Knudson et al. . |
| 5,830,222 | 11/1998 | Makower . |

OTHER PUBLICATIONS

Kashem, M., "Feasibility Study of Left Ventricle to Coronary Artery Perfusion for Severe Coronary Artery Diseases", *ASAIO Journal*, vol. 45, No. 2, 2 pages (Mar.–Apr. 1999).

*Primary Examiner*—Dinh X. Nguyen
(74) *Attorney, Agent, or Firm*—Merchant & Gould P.C.

(57) ABSTRACT

A blood flow path is formed from a heart chamber to a coronary vessel. The coronary vessel has a predetermined diameter. A hollow conduit is selected having a vessel portion and a myocardial portion. The vessel portion has an open leading end sized to be inserted into the coronary vessel. The myocardial portion has an open leading end and the myocardium portion is sized to extend through a thickness of the heart wall. The conduit is selected with the vessel portion sized to be inserted within the vessel without dilating the vessel to such a degree that the vessel is incapable of further dilation in response to blood flow in the vessel. The myocardial portion is placed in the heart wall with the open leading end of the myocardial portion protruding into the heart chamber. The leading end of the vessel portion is placed in the coronary vessel. The vessel is secured to the vessel portion by urging the vessel against the vessel portion at a point of attachment spaced from the open leading end of the vessel portion.

6 Claims, 2 Drawing Sheets

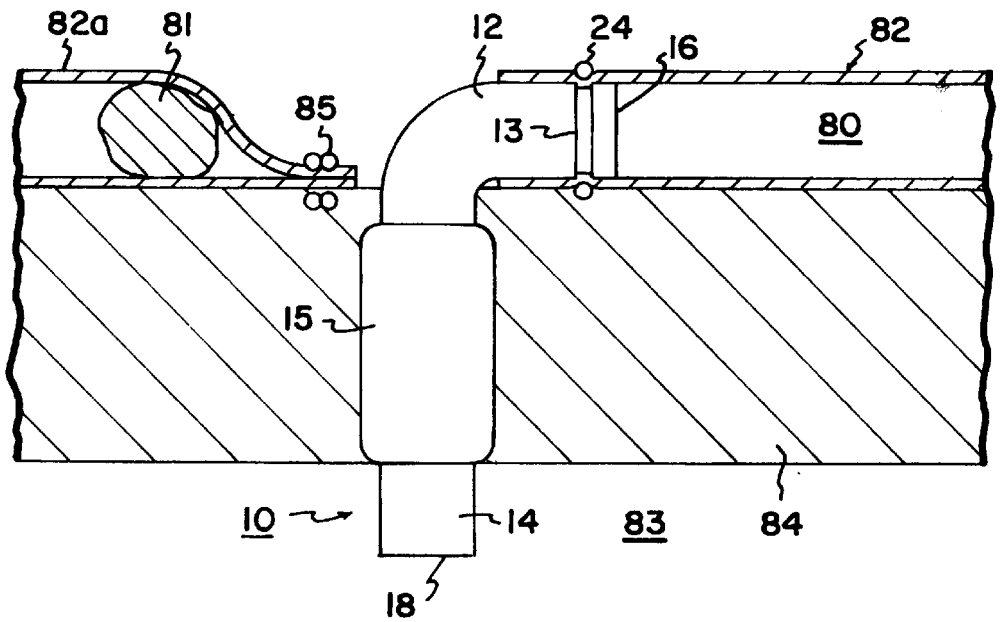
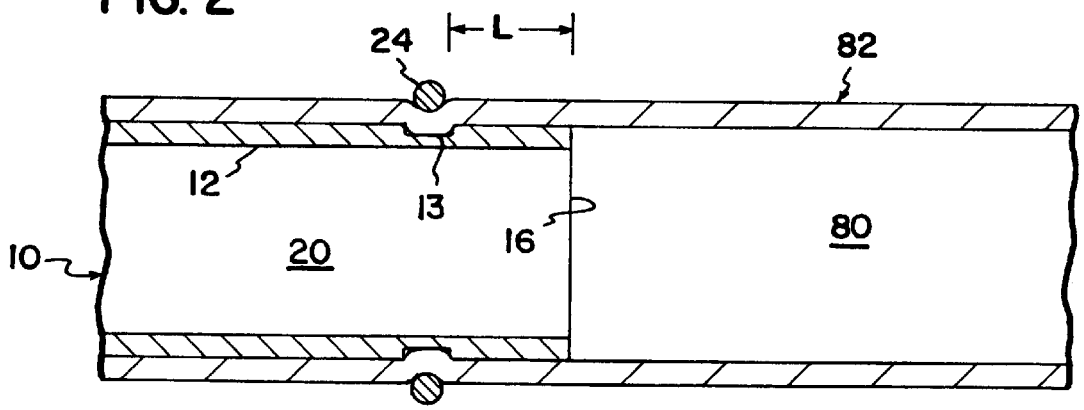
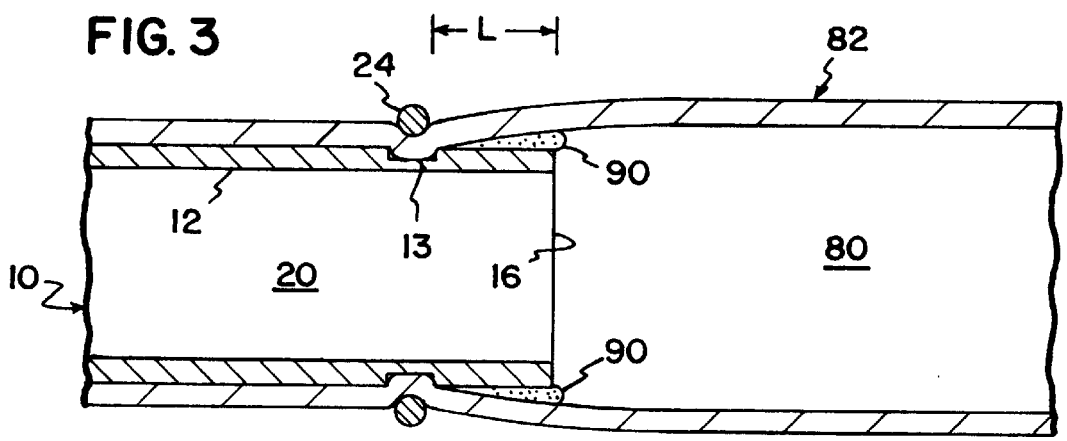

TRANSMYOCARDIAL IMPLANT WITH INDUCED TISSUE FLAP

BACKGROUND OF THE INVENTION

1. Field of the Invention

The present invention pertains to cardiac revascularization and more particularly to a procedure for cardiac revascularization involving forming a blood flow path through a heart wall from a heart chamber to a coronary vessel.

2. Description of the Prior Art

Commonly assigned U.S. Pat. No. 5,755,682 and co-pending and commonly assigned U.S. patent application Ser. No. 08/882,397 now U.S. Pat. No. 5,944,019 filed Jun. 25, 1997 (also filed as international application Ser. No. PCT/US97/13980 published as PCT WO 98/06356) teach an implant for defining a blood flow conduit directly from a chamber of the heart to a lumen of a coronary vessel. An embodiment disclosed in the aforementioned application teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced patent application, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997 (filed internationally as PCT Ser. No. PCT/US98/17310 published as WO 99/17683) entitled "Transmyocardial Implant" teaches an implant such as that shown in the aforementioned '682 patent '397 application with an enhanced fixation structure. One embodiment of the enhanced fixation structure includes a fabric surrounding at least a portion of the conduit to facilitate tissue growth on the exterior of the implant.

Implants such as those shown in the aforementioned patent applications include a portion to be placed within a coronary vessel and a portion to be placed within the myocardium. When placing a portion of the implant in the coronary artery or other coronary vessel, the artery is incised by an amount sufficient to insert the implant. Preferably, the artery is ligated distal to an obstruction. A transverse incision is made through the artery distal to the ligation. Tools and procedures for such an implantation are shown and described in commonly assigned and copending U.S. patent application Ser. No. 09/063,160 filed Apr. 20, 1998.

In the foregoing references, a constantly open blood flow path is preferred. However, the references also teach a conduit with a valve which closes during diastole. The afore-mentioned PCT/US97/13980 teaches a conduit with a valve which only partially closes during diastole to permit a washing back-flow.

Conduits which include a valve or which otherwise close during the heart cycle are shown in U.S. Pat. No. 5,287,861; U.S. Pat. No. 5,409,019 and 5,429,144 (all to Wilk) and PCT International Publication Nos. WO 98/08456 and WO 98/46115. The alleged benefits of a valve in such a conduit are described in Kashem et al., "Feasibility Study of Left Ventricle to Coronary Artery Perfusion for Severe Coronary Artery Diseases", ASAIO Journal, Vol. 45, No. 2 (March-April, 1999) (Abstract).

Valves in such conduits are difficult to manufacture. For example, such conduits may have internal diameters of 2.0 mm or smaller. The presence of such small valves increase the probability of thrombus.

While a constantly open blood flow path is a presently preferred embodiment which affords amble net forward flow to revascularize the heart, a valve or other structure which at least partially retards retrograde flow during diastole may improve flow. The present invention is directed toward a method of attaining the function and benefits of a valve without the need to fabricate a valve. As will be more fully described, the present invention is directed to a novel implantation technique which induces a tissue response to grow a tissue flap which behaves like a valve.

SUMMARY OF THE INVENTION

According to a preferred embodiment of the present invention, a method is disclosed for forming a blood flow path from a heart chamber to a coronary vessel. The coronary vessel has a predetermined diameter. The method includes selecting a hollow conduit having a vessel portion and a myocardial portion. The vessel portion has an open leading end sized to be inserted into the coronary vessel. The myocardial portion has an open leading end and the myocardium portion is sized to extend through a thickness of the heart wall. The conduit is selected with the vessel portion sized to be inserted within the vessel without dilating the vessel to such a degree that the vessel is incapable of further dilation in response to blood flow in the vessel. The myocardial portion is placed in the heart wall with the open leading end of the myocardial portion protruding into the heart chamber. The leading end of the vessel portion is placed in the coronary vessel. The vessel is secured to the vessel portion by urging the vessel against the vessel portion at a point of attachment spaced from the open leading end of the vessel portion.

BRIEF DESCRIPTION OF THE DRAWINGS

FIG. 1 is a side schematic view showing an implant in place with a heart wall and coronary vessel shown in cross-section;

FIG. 2 is an enlarged cross-sectional view of a vessel portion of the implant of FIG. 1 placed in a coronary vessel at the time of placement;

FIG. 3 is the view of FIG. 1 following an initial period of time for a tissue response to initiate;

DESCRIPTION OF THE PREFERRED EMBODIMENT

Figure 4:
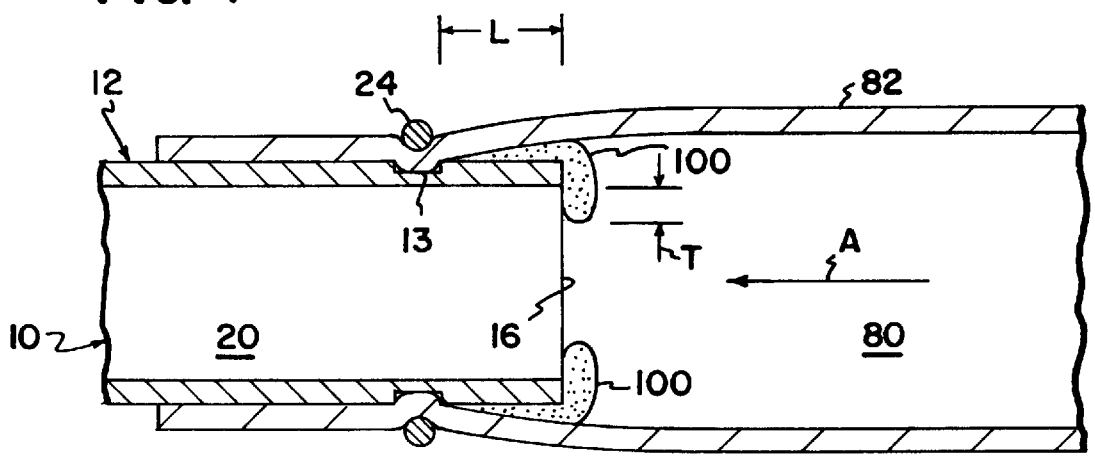
FIG. 4 is the view of FIG. 3 following an additional period of time for the tissue response to fully develop to create a flap only partially covering the open end of the vessel portion during diastole to partially obstruct retrograde flow from the vessel into the heart.

With initial reference to FIG. 1, a conduit 10 is shown in the form of an L-shaped tube. The conduit 10 is preferably formed of titanium but may be other biocompatible material. The material of the conduit 10 is preferably radially rigid in order to withstand contraction forces of the myocardium. By way of non-limiting example, the conduit 10 will have an outside diameter of about 2.5 millimeters and an internal diameter of about 2.0 millimeters to provide a wall thickness of about 0.5 millimeters. As will be more fully described, the size of the conduit 10 is sized to match a vessel. Coronary arteries requiring bypass typically have diameters ranging from 4.0 mm to 1.0 mm and the appropriately sized conduit 10 is selected to match the vessel.

The tube 10 has a vessel or coronary portion 12 sized to be received within the lumen of a coronary vessel such as the lumen 80 of a coronary artery 82 distal to an obstruction 81 as illustrated in FIG. 1. The coronary portion 12 has a coronary opening 16 to discharge blood axially into the vessel lumen 80. A groove 13 is formed around the vessel portion 12 spaced a distance L from the coronary opening 16.

The conduit 10 has a myocardial portion 14 extending at a right angle to the axis of portion 12. The myocardial portion 14 is sized to extend from the coronary artery 82 directly through the myocardium 84 and protrude into the left ventricle 83 of a patient's heart.

A fabric cuff 15 surrounds the myocardial portion 14. The cuff 15 permits integration of the myocardium 84.

The myocardial portion 14 has a myocardial opening 18 in communication with an interior 20 of the implant 10. Therefore, blood can freely flow through the implant 10 between the left ventricle 83 and the lumen 80 of the coronary artery 82. Blood flows out of discharge opening 16 at a discharge axis parallel with the axis of lumen 80.

The longitudinal axis of the coronary portion 12 is aligned with the axis of the lumen 80. A suture 24 surrounds the artery 82 over the groove 13 to secure the artery 82 to the coronary portion 12. The proximal portion 82a of the coronary artery is ligated by sutures 85. A surgical procedure for placing a conduit 10 and tools for such procedure are more fully described in commonly assigned and co-pending U.S. patent application Ser. No. 09/063,160 filed Apr. 20, 1998. Preferably, the patient will be on an anti-platelet drug therapy such as aspirin, triclopidine, clopidogrel or GPI-IbIIIa antagonists (so-called "super aspirins").

The conduit 10 is sized to be inserted into the lumen 80 without undue dilation of the artery 82. While damage to endothelial cells is unavoidable, it is desired to avoid damage to the structural architecture of the artery 82 (e.g., to avoid damage the internal elastic lamina of the artery 82). As will become apparent, by avoiding undue dilation of the artery 82, the artery 82 is free to expand in response to blood pressure within the artery 82 and define an annular space between the artery 82 and the conduit 82 distal to the stay suture 24. Also, avoidance of undue dilation avoids hyperplastic response of a damaged artery.

To avoid undue dilation, the diameter of the artery 82 (on a beating heart) is sized prior to implantation of the conduit 10. The internal diameter can be measured or otherwise sized through angiography, ultrasonography or other method. Alternatively (but less desirable), the artery internal diameter can be approximated by measuring the outside diameter of the artery 82 and assuming a wall thickness (e.g., about 0.5 mm).

With the predetermined artery internal diameter, the conduit 10 is selected for the outside diameter of the conduit 10 to not over-dilate the artery 82 as described above. Preferably, the conduit 10 is sized so that after implantation, the artery 82 is not so dilated that it cannot further expand in response to blood pressure. To insure such remaining flexibility, the conduit 10 is preferably sized to have a diameter the same as or less than the internal diameter of the artery 82. With the given example, a 2.5 mm outside diameter implant 10 is used in an artery having an inside diameter of 2.5 mm to 3.0 mm. For larger arteries, a larger conduit 10 is used. Preferably, the artery inside diameter is no more than 0.5 mm to 1.0 mm larger than the outside diameter of the conduit 10. While the upper limit of 1.0 mm is not necessary to practice the invention, selecting too small of a conduit 10 unnecessarily restricts the amount of blood which can flow through the conduit 10 into the artery 82.

As shown in a preferred embodiment, the artery 82 is urged against the exterior of the vessel portion 12 by a stay suture 24 surrounding the artery 82 over the groove 13. The suture 24 urges the artery 82 to be compressed in the groove 13 to insure the suture 24 does not migrate relative to the conduit 10. The single suture 24 results in a length L of artery 82 from the groove 13 to the free end 16 being unsupported and free to dilate in response to blood pressure within the artery 82. As an alternative to stay suture 24, any other method (e.g., a collar around the artery 82) could be used to urge the artery 82 against the vessel portion 12 while leaving a length L free to dilate. In a preferred embodiment, length L is 1.0 mm but could be up to 3.0 mm.

As a result of free length L and the ability of the artery 82 to dilate following implantation, an annular space forms between the vessel portion 12 and artery 82 in length L. This space is a region of stagnant blood flow. Such regions are sites of thrombus formation 90 (FIG. 3).

While thrombus formation is normally considered undesirable, the present invention utilizes such thrombus formation to create a natural valve. Namely, in porcine surgeries, it has been discovered that such thrombus formation organizes into structural tissue in the form of a flap 100 only partially covering the open free end 16. Histological studies of porcine models following surgery according to the present invention show the formation of a flap 100 of organized structural cells (e.g., fibroblasts) covered by pseudoendothelium which is at a steady-state development after about 2–4 weeks. In humans, such steady-state response is anticipated to occur after about 4–8 weeks. The histological response shows such flap 100 extends a distance T about 0.25 mm radially inward from the interior surface of the conduit 10.

Figure 5:
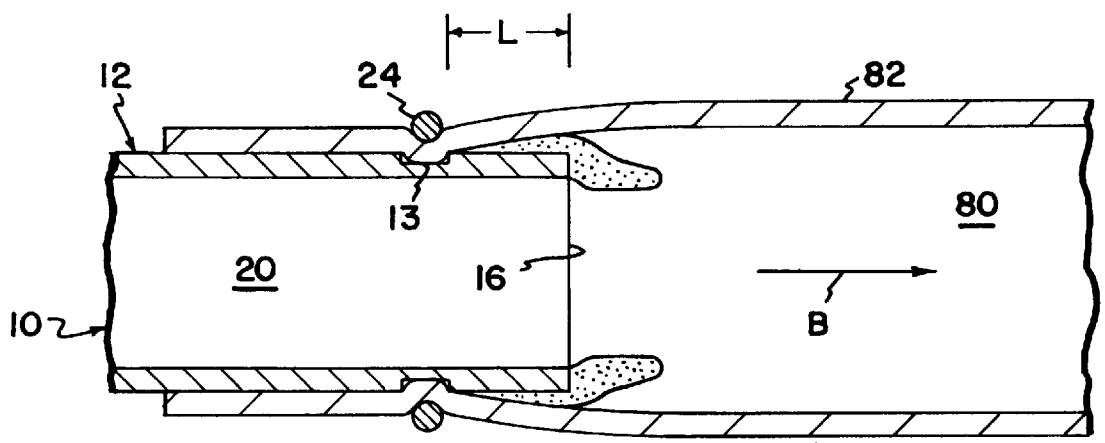
FIG. 5 is the view of FIG. 4 showing the flexible flap fully open in response to blood flow during systole to permit unobstructed flow from the conduit into the vessel.

The flap 100 is flexible. During systole, when blood is flowing out of open end 16 in the direction of arrow B in FIG. 5, the flap 100 is urged by blood flow to extend into the artery lumen 80 thereby providing no substantial interference to blood flow. During diastole, blood tends to flow in the direction of arrow A in FIG. 4 into the conduit 10 from the lumen 80. In response to such flow, the flap 100 partially covers open end 16 thereby impeding such retrograde flow. As a result, blood flows more freely in the forward direction (arrow B) than in the retrograde direction (arrow A). This results in improved net forward flow.

The tissue response creating flap 100 can be further induced by coating the exterior of the conduit 10 in length L with a growth inducing substance. For example, a bioabsorbable substrate can be placed in this region. Such a substrate can be a porous resorbable polymer which acts as a matrix to hold a clot and promote growth of the structure of the flap 100. Such substances may include collagen or PLA (polylactic acid), PGA (polyglycolic acid) or copolymers of the latter two.

With the present invention, the benefits of a valve are achieved without having a thrombogenic valve introduced into the conduit 10. The flap 100 produced by the present invention is the patient's natural tissue which is blood compatible.

Having disclosed the present invention in a preferred embodiment, it will be appreciated that modifications and equivalents may occur to one of ordinary skill in the art having the benefits of the teachings of the present invention.

It is intended that such modifications shall be included within the scope of the claims appended hereto.

What is claimed is:

1. A method for forming a blood flow path from a heart chamber to a coronary vessel on an exterior surface of a heart wall, the coronary vessel having a predetermined diameter, the method comprising:

selecting a hollow conduit having a vessel portion and a myocardial portion, the vessel portion having an open leading end sized to be inserted into the coronary vessel, the myocardial portion having an open leading end and the myocardium portion being sized to extend through a thickness of the heart wall;

selecting said conduit with said vessel portion sized to be inserted within said vessel without dilating said vessel to such a degree that said vessel is incapable of further dilation in response to blood flow in said vessel placing the myocardial portion in the heart wall with the open leading end of the myocardial portion protruding into the heart chamber;

placing the leading end of the vessel portion in the coronary vessel;

securing said vessel to said vessel portion by urging said vessel against said vessel portion at a point of attachment spaced from said open leading end of said vessel portion.

2. A method according to claim 1 wherein said vessel portion is sized to avoid dilation of said vessel below a degree of dilation which would substantially damage an internal elastic lamina of said vessel.

3. A method according to claim 1 wherein said vessel remains detached from said vessel portion between said point of attachment and said open leading end of said vessel portion.

4. A method according to claim 3 wherein said vessel portion has a wall thickness at said open leading end less than a thickness of a tissue flap to be grown in response to placement of said vessel portion in said vessel.

5. A method according to claim 1 wherein said vessel portion is placed in said vessel to induce growth of a tissue flap only partially covering said open leading end of said vessel portion.

6. A method according to claim 1 wherein said vessel portion is treated with substances to promote tissue growth in an annular space between the vessel portion and the vessel.

* * * * *